United States Patent [19]

Kise et al.

[11] Patent Number: 5,015,636
[45] Date of Patent: May 14, 1991

[54] THIAZETIDINE COMPOUNDS

[75] Inventors: Masahiro Kise, Nakakyo; Masakuni Ozaki, Joyo; Kenji Kazuno, Shiga; Yoshifumi Tomii, Katano; Jun Segawa, Minami; Shoji Yasufuki, Nishikyo, all of Japan

[73] Assignee: Nippon Shinyaku Co., Ltd., Japan

[21] Appl. No.: 388,854

[22] Filed: Aug. 3, 1989

Related U.S. Application Data

[62] Division of Ser. No. 247,959, Sep. 22, 1988, Pat. No. 4,882,328.

[30] Foreign Application Priority Data

Sep. 22, 1987 [JP] Japan .................. 62-237729

[51] Int. Cl.⁵ ................. C07D 513/12; A61K 31/505; A61K 31/535
[52] U.S. Cl. ...................... 514/210; 514/233.2; 514/254; 514/267; 540/116; 540/250
[58] Field of Search ................. 544/250, 115; 514/267, 514/233.2, 254, 210

[56] References Cited

U.S. PATENT DOCUMENTS 4,843,070 6/1989 Kise et al. .................. 514/210

Primary Examiner—Mukund J. Shah
Assistant Examiner—Jyothsna Denkat
Attorney, Agent, or Firm—Jacobs & Jacobs

[57] ABSTRACT

Compounds of the formula

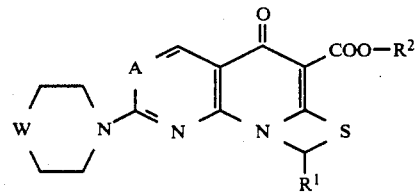

and pharmaceutically acceptable salts thereof, $R^1$ is hydrogen, alkyl or aryl unsubstituted or substituted by one or two halo moieties, $R^3$ is hydrogen or alkyl, A is N, W is O or $NR^3$ wherein $R^3$ is hydrogen, alkyl, acyl, haloacyl, 2alkoxycarbonyl or (5-methyl-2-oxo-1,3-dioxolen-4-yl) methyl are useful for treating bacterial infections in humans and animals.

27 Claims, No Drawings

THIAZETIDINE COMPOUNDS

CROSS-REFERENCE

This is a division of Ser. No. 247,959 filed Sept. 22, 1988, now U.S. Pat. No. 4,882,328.

The present invention is concerned with thiazetidine derivatives which are useful for their antibacterial activity.

It is known to treat gram-negative bacterial infections with such agents as nalidixic acid, pyromidic acid, pipemidic acid, enoxacin (AT-2266), ofloxacin (DL-8280) inter alia. However, none of these provides satisfactory treatment for chronic infections caused by *Pseudomonas aeruginosa* or gram-positive bacterial infections caused by more virulent gram-positive bacteria.

The present invention is based on the discovery that thiazetidine derivatives are particularly useful for treating gram-negative bacterial infections such as *Pseudomonas aeruginosa* and gram-positive bacterial infections. More particularly, the present invention is concerned with thiazetidine derivatives of the formula

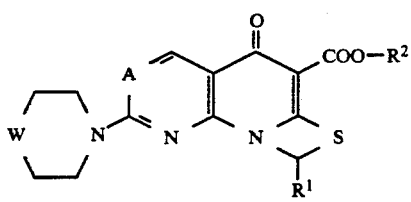

(I)

and pharmaceutically acceptable salts thereof wherein $R^1$ is hydrogen, alkyl, preferably lower alkyl, or aryl, preferably phenyl unsubstituted or substituted by one or two halo moieties, $R^2$ is hydrogen or alkyl, preferably lower alkyl, A is N or CX wherein X is halo, W is O or $NR^3$ wherein $R^3$ is hydrogen, alkyl, preferably lower alkyl, acyl, haloacyl, alkoxycarbonyl, preferably lower alkoxycarbonyl or (5-methyl-2-oxo-1,3-dioxolen-4-yl) methyl. The compounds have been found to be particularly useful for their antibacterial activity and are thus useful for the treatment of bacterial infections both caused by gram-negative and by gram-positive bacteria. Because of their low toxicity, they are useful for treating such infections in humans and animals.

According to one embodiment of the present invention, the alkyl group of $R^1$, $R^2$ and $R^3$ is straight or branch chain alkyl preferably of 1 to 6 carbon atoms for example, methyl, ethyl, n-propyl, isopropyl, n-butyl, isobutyl, sec-butyl, tert-butyl, n-pentyl, isopentyl, n-hexyl and isohexyl.

According to another embodiment of the present invention, the aryl moiety of $R^1$ is preferably phenyl which is either unsubstituted or substituted by 1 or 2 halo substituents, particularly by fluoro, especially difluoro. Particularly preferred substituents for $R^1$ are phenyl, 4-fluorophenyl, 2,4-diflurophenyl, 3,4-difluorophenyl and 3,5-difluorophenyl.

According to a further embodiment of the present invention, the acyl moiety of $R^3$ is a straight or branch chain moiety having from 1 to 6 carbon atoms such as for example, formyl, acetyl, propionyl, n-butyryl, isobutyryl, valeryl, isovaleryl, pivaloyl and n-hexanoyl or haloacyl such as mono-, di- or tri-halo substituted acyl especially trifluoroacetyl.

The alkoxycarbonyl group of $R^3$ is a straight or branch chain moiety preferably of 2 to 5 carbon atoms for example, methoxycarbonyl, ethoxycarbonyl, n-propoxycarbonyl, isopropoxycarbonyl and n-butoxycarbonyl.

The halo moieties of X are chloro, bromo, fluoro and iodo preferably chloro or fluoro.

When the compounds of the present invention are in the form of pharmaceutically acceptable salts, they are preferably salts of mineral acids such as the hydrochloride, sulfate, nitrate, phosphate, hydrofluoride, hydrochloride or salts or organic acids such as formate, acetate, tartrate, lactate, citrate, fumarate, maleate, succinate, methanesulfonate, ethanesulfonate, benzenesulfonate, toluenesulfonate, naphthalenesulfonate or camphorsulfonate. Pharmaceutically acceptable salts according to the present invention also include salts of alkali metals or alkaline earth metals such as sodium, potassium, calcium and the like. The compounds of the present invention are produced in accordance with the following methods.

Method-A:

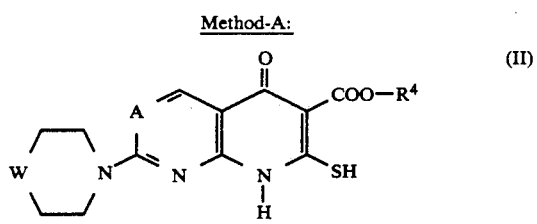

(II)

In the above reaction, $R^1$, A and W are as above defined with respect to formula (I). Y and Z are the same or different and each is halo. $R^4$ is alkyl, especially lower alkyl.

Method-B:

(II) $\xrightarrow{ZCH_2-R^1}$

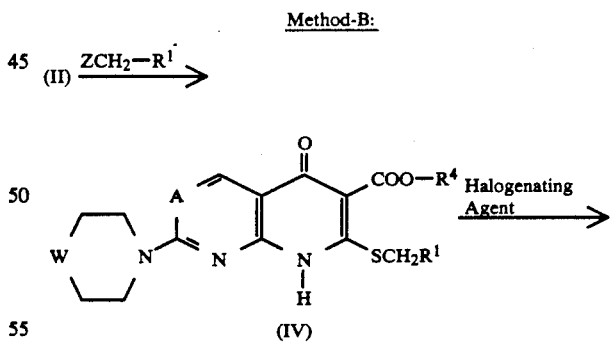

(IV)

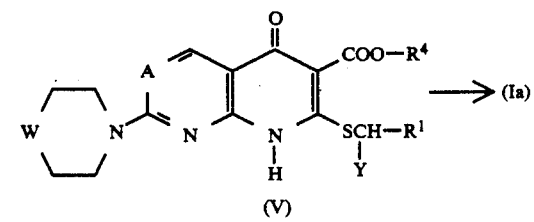

(V)

$\longrightarrow$ (Ia)

In the above reaction, $R^1$, $R^4$, A, W, Y and Z are as above defined with respect to Method-A.

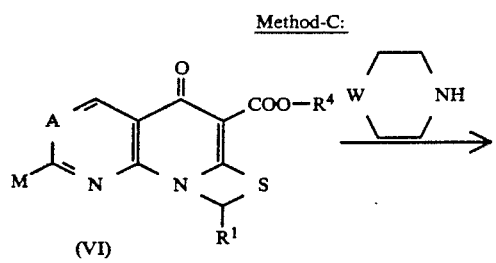

Method-C:

(VI) → (Ia)

In the above reaction, $R^1$, $R^4$, A and W are as above defined with respect to Method-A. M is halo or alkylsulfinyl, especially lower alkylsulfinyl.

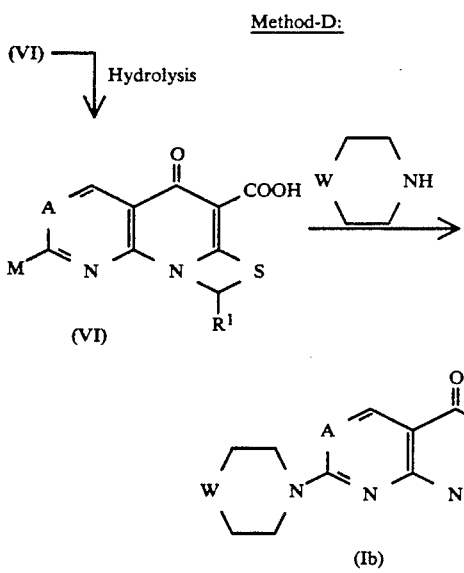

Method-D:

(VI) —Hydrolysis→ (VI) → (Ib)

In the above reaction, $R^1$, A and W are as above defined with respect to Method-A. M is halo or alkylsulfinyl, especially lower alkylsulfinyl.

As can be seen from above Methods-A through D, the compounds of the present invention can be produced by two typical reaction routes. According to one route, a thiazetidine ring is formed from a starting material of a naphthyridine-carboxylic acid or pyridopyrimidine-carboxylic acid substituted by a morpholine moiety or a substituted or unsubstituted piperazine moiety (hereinafter referred to as an "amine": Method A and Method B). According to the other process a thiazetidine ring is formed followed by the introduction of an amine into the ring-containing compound (Method C and Method D). These four processes will be discussed in more detail below.

Method-A

Compound II is reacted with a dihalide (for example, methylene iodide, ethylidene bromide, benzylidene bromide) in a solvent which is inert to the reaction, in the presence of a base for example, sodium carbonate, potassium carbonate, triethylamine or the like, generally at a temperature of from about 0° C. to about 120° C. for the purpose of preparing the cyclized compound Ia.

Suitable solvents are aprotic solvents such as N,N-dimethylformamide, N,N-dimethylacetamide, dimethylsulfoxide or sulforan. The amount of dihalide and base to be used is preferably from 1.1 to 2.5 mols per mol of compound II. In order to accelerate the reaction, sodium iodide or potassium iodide (0.01 to 3.0 molar equivalents) may be added to the reaction.

Method-B

Compound II and a halide ($ZCH_2$—$R^1$) are reacted, using the same reaction solvent and base as those described in the Method-A, generally at a temperature of from about 0° C. to 80° C. to prepare compound IV. Thereafter, the resulting compound IV is halogenated with a suitable halogenating agent (for example, N-bromo-succinimide, N-chlorosuccinimide or the like) in an inert solvent (for example, halogenated hydrocarbon solvents such as chloroform, dichloromethane or carbon tetrachloride), to prepare compound V. Compound V is cyclized, using the same reaction solvent and base as those described in the Method-A, generally at a temperature of from about 0° C. to about 80° C. to prepare compound Ia.

Method-C

Compound VI is condensed with an amine to prepare compound Ia. In accordance with this process, compound VI is reacted with an amine in a suitable solvent which is inert to the reaction (for example, aprotic solvents such as N,N-dimethylformamide, N,N-dimethylacetamide, dimethylsulfoxide, sulforan, acetonitrile), and optionally in the presence of a base (such as sodium carbonate, potassium carbonate, sodium hydrogencarbonate, potassium hydrogencarbonate or triethylamine) generally at a temperature of from about 0° C. to about 80° C., for example at 40° C. to 60° C. The amount of the amine to be used is from 1.5 to 2.5 mols per mol of compound VI.

Method-D

Compound VI is hydrolyzed with an acid (for example, concentrated sulfuric acid, fuming sulfuric acid, polyphosphoric acid or a mixture thereof) to prepare compound VII. The reaction is carried out in the presence of an excess amount (one to 30 times by weight, preferably 5 to 10 times by weight) of an acid as a solvent, generally at a temperature of from about 0° C. to about 60° C. The hydrolyzing reaction may also be carried out in 20 to 30 times by weight (preferably 5 to 10 times by weight) of a 1% to 5% potassium hydroxide or sodium hydroxide-containing aqueous alcohol (e.g., methanol, ethanol, propanol, butanol, preferably tert. butanol), generally at about room temperature to about 60° C.

Next, compound VII is reacted with an amine in the same solvent as that used in the Method-C to prepare compound Ib. The reaction is carried out generally at a temperature of from about 0° C. to about 60° C., preferably at 0° C. to room temperature.

According to a further method of the present invention, the compounds of the formula I can also be obtained from a compound of the formula VIII in accordance with reaction scheme set forth below:

Method-E

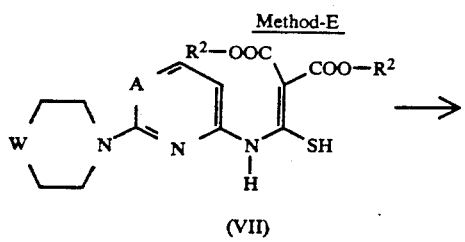

(VII)

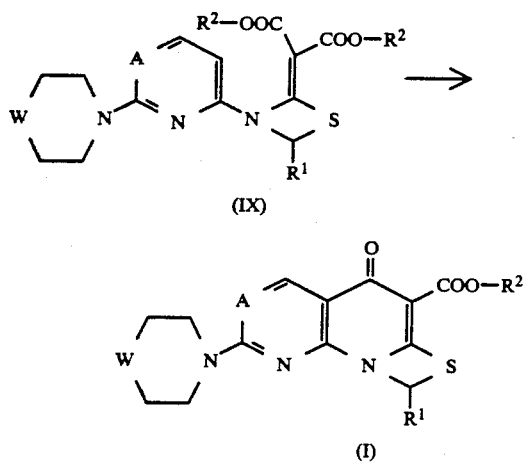

(IX)

↓

(I)

In the above reaction, $R^1$, $R^2$, A and W, are as defined with respect to formula I.

More particularly, compound VIII is reacted with a dihalide in the presence of a base (for example, potassium carbonate) in an inert solvent (for example, N,N-dimethylformamide). That reaction may be carried out in a manner analogous to that described above with respect to Method-A. Thereafter, compound IX is subjected to a ring closing reaction which is carried out by techniques per se known to produce compounds of the formula I. For example, acidic substances such as phosphorus oxychloride, phosphorus pentachloride, phosphorus trichloride, thionyl chloride, fuming sulfuric acid, concentrated sulfuric acid, polyphosphoric acid, polyphosphoric acid esters or the like may be used.

When an acidic substance is used, the amount of the acidic substance to be used for the process is from one mole to a large excess amount, preferably from 20 to 30 mole per moles of compound IX. The reaction is generally carried out at temperature of from about 0° C. to about 100° C., preferably at 0° C. to 60° C.

Dependent upon the acidic substance used and the reaction conditions, the ester moiety of compound IX may be hydrolyzed along with the ring closure.

When a piperazine is used in the above reaction, one nitrogen atom of the piperazine compound may optionally be protected with a suitable protective group for example, an acyl group, by techniques per se known, if desired, and the final product obtained thereafter may have the protective group, or alternatively the protective group may be removed so as to form a final product which does not contain the protective group. The removal of the protective group may also be carried out by procedures per se known.

In addition, an N-unsubstituted product may be processed by methods per se known so as to introduce a substituent onto the nitrogen atom to give an N-substituted piperazine compound.

Other methods per se known may be used to carry out the N-alkylation, which includes reaction with a halogenated alkyl moiety, a reaction with an ester of alkylsulfuric acid such as dimethylsulfuric acid or a sulfonic acid, or a reductive alkylating reaction with an aldehyde. The reaction conditions for the respective reactions vary in accordance with the kinds of the reactants and the alkylating agents used, and reaction temperature, reaction time and the solvent selected.

When the moiety (5-methyl-2-oxo-1-,3-dioxolen-4-yl) methyl is to be introduced onto the nitrogen atom, the following method, is suitable:

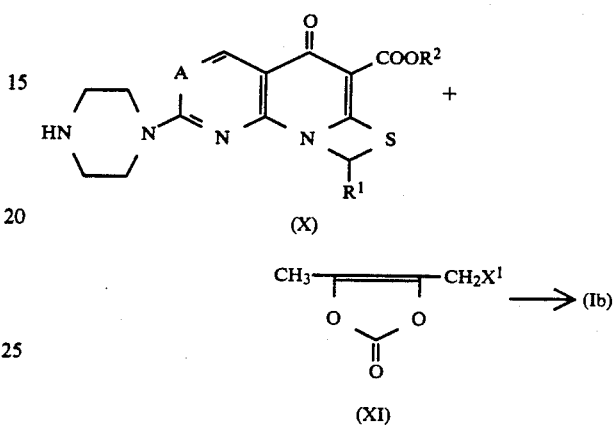

wherein A, $R^1$ and $R^2$ are as above defined and $X^1$ is halo.

Thus, the compounds of the forumlae X and XI are reacted in the absence or presence of an inert solvent in the presence of a base (such as sodium carbonate, potassium carbonate, sodium bicarbonate, potassium bicarbonate, triethylamine, etc.) usually at a temperature of from about −20° C. to about +80° C. (most preferably at −5° C. to ambient temperature) to produce compounds of the formula Ib.

Preferred solvents used are aprotonic ones such as, for example, N,N-dimethylformamide, dimethyl sulfoxide, and ethers including diglyme.

The amount of compound XI to one mole of compound X is preferably equimolar to an excess. The reaction time may vary depending upon the types and amounts of starting materials, solvents and bases as well as reaction temperature but, usually, it may be from about 2 to 20 hours.

When the compounds of the present invention are produced in ester form, these may optionally be hydrolyzed, if desired, to convert them into the corresponding free carboxylic acids (that is, $R^2$ in formula I is hydrogen). The hydrolysis reaction is carried out with a large excess amount of an acid (for example, sulfuric acid, fuming sulfuric acid, hydrochloric acid, hydrobromic acid, hydrobromic acid/acetic acid, chlorosulfonic acid, polyphosphoric acid), preferably using the acid in an amount of from 10 to 20 times by weight as a solvent, at from about room temperature to about 110° C. The esters may also be hydrolyzed in 20 to 30 times by weight (preferably 5 to 10 times by weight) of a 1% to 5% potassium hydroxide or sodium hydroxide-containing aqueous alcohol (e.g., methanol, ethanol, propanol, butanol, preferably tert.butanol) solvent, at from about room temperature to about 60° C. with stirring.

The esters of the present invention, that is, those wherein $R^2$ is alkyl may be transesterified, that is, one ester may be converted to a different ester, for example, by heating the ester in 10 to 100 times of an alcohol which corresponds to the intended ester to be formed by the transesterification in the presence of a catalytic amount of concentrated sulfuric acid, while stirring at a temperature of from about 60° C. to about 150° C., preferably at about 100° C. to about 110° C.

When the compounds obtained are in the form of the acid that is $R^2$ in formula I is hydrogen, such compounds may if desired be esterified. The esterification reaction can be carried out in accordance with well known esterification procedures, for example, by the use of thionyl chloride in an alcohol, an alcohol and a condensing agent (e.g., dicyclocarbodiimide), or an alkyl halide and an alcoholate. In addition, the carboxylic acids may be converted into pharmaceutically acceptable salts such as for example, the sodium and potassium salts by techniques known per se and such salts may also be converted to the corresponding free acids.

Starting compounds II and VIII may be prepared by those skilled in the art using known methods. Preferred processes are described in Japanese Application JP-A-59-227887 and JP-A-59-210093 which are specifically incorporated herein by reference.

Starting compound VI is new and may be prepared in accordance with Methods-A and B described above. Example A below more particularly illustrates the preparation of a representative compound of formula VI.

The final products of formula I thus may be isolated and purified by procedures per se known, for example, by concentration, liquid conversion, conversion dissolution, solvent extraction, crystallization, recrystallization, fractional distillation, chromatography and the like.

When the compounds of the present invention are administered as pharmaceuticals, to humans and animals, they are given per se or as a pharmaceutical composition containing, for example, 0.1 to 99.5% (more preferably, 0.5 to 90%) of active ingredient in combination with a pharmaceutically acceptable carrier.

The compounds of the present invention may be given orally, parenterally, topically, or rectally. They are of course given by forms suitable for each administration route. For example, they are administered in tablets or capsule form, by eye lotion, ointment, suppository, etc. administration by injection, infusion or inhalation; topical by lotion or ointment; and rectal by suppositories. Oral administration is preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginage, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically accetable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the dosage for treating bacterial infections a number of factors such as the age of the patient, body weight, severity of condition, administration route, and the like must be considered. Generally, from about 50 mg to 1 g per day of a compound of the present invention should be administered to a human adult preferably from 100 mg to 300 mg per day orally. In some cases, a lower dose is sufficient and, in some other cases, a higher dose or more doses may be necessary. The administration may be one to several times a day or with an intermission of one to several days.

It is preferred that the administration be divided so that administration takes place 2 or 3 times per day.

The following nonlimitative examples more particularly illustrate the present invention.

EXAMPLE A (1) Ethyl 1-methyl-7-methylthio-4-oxo-4H[1,3]thiazeto[3',2'-1,2]pyrido[2,3-d]pyrimidine-3-carboxylate 5.58 g of potassium carbonate, 18.95 g of ethylidene bromide and 0.34 g of potassium iodide were added to 160 ml of dry N,N-dimethylformamide (DMF) and heated at 115° C. (bath temperature) for 10 minutes. A solution of 6.00 g of ethyl 5-hydroxy-2-methylthio-7-thioxo-7,8-dihydro-pyrido[2,3-d]pyrimidine-6-carboxylate was dissolved in 400 ml of dry DMF was dropwise added thereto over a period of 1 hour. The whole solution was stirred for an additional 7 hours at the same temperature. The insoluble substances were taken out by filtration and the solvent was taken out by distillation under reduced pressure. The residue was partitioned in chloroform/water, extracted two times with chloroform and washed with an aqueous saturated salt solution. The extract was dried with magnesium sulfate and the solvent was removed by distillation. The residue was recrystallized from ethanol to obtain 4.33 g of the intended compound. m.p. 206° to 207° C.

Elementary Analysis ($C_{13}H_{13}N_2O_3S_2$): Calculated Value (%) C: 48.28, H: 4.05, N: 12.99. Measured Value (%) C: 48.11, H: 3.98, N: 12.93.

(2) 1-Methyl-7-methylthio-4-oxo-4H[1,3]thiazeto[3',2'-1,2]pyrido[2,3-d]pyrimidine-3-carboxylic acid:

4.10 g of the compound obtained in the above-mentioned step (1) was dissolved in 50 ml of fuming sulfuric acid and stirred at 60° C. (bath temperature) for 60 minutes. The reaction solution was poured onto ice and the precipitate formed was collected by centrifugation. This was washed with water, methanol and ether each three times and dried under reduced pressure to obtain 3.40 g of the intended compound. m.p. 225° to 227° C. (decomposition).

Elementary Analysis ($C_{11}H_9N_3O_3S_2$): Calculated Value (%) C: 44.74, H: 3.07, N: 14.23. Measured Value (%) C: 44.74, H: 2.93, N: 14.12.

(3) 1-Methyl-7-methylsulfinyl-4-oxo-4H[1,3]thiazeto[3',2'-1,2]pyrido[2,3-d]pyrimidine-3-carboxylic acid:

1.00 g of the compound obtained in the above-mentioned step (2) was dissolved in 250 ml of chloroform, and 0.77 g of m-chloro-perbenzoic acid (m-CPBA) was gradually added thereto. After stirring for 1 hour, the solvent was removed by distillation under reduced pressure. The residue was washed with ethanol and ether and dried under reduced pressure to obtain 0.98 g of the intended compound. m.p. 208° to 210° C. (decomposition).

Elementary Analysis ($C_{11}H_9N_3O_4S_2$) Calculated Value (%) C: 42.44, H: 2.91, N: 13.50. Measured Value (%) C: 41.83, H: 3.03, N: 13.30.

In the same manner, the following compounds were obtained.

7-Methylsulfinyl-4-oxo-4H[1,3]thiazeto[3',2'-1,2]pyrido[2,3-d]pyrimidine-3-carboxylic acid:

m.p. 300° C. or higher.

Elementary Analysis ($C_{10}H_7N_3O_4S_2$) Calculated Value (%) C: 40.40, H: 2.37, N: 14.13. Measured Value (%) C: 40.06, H: 2.17, N: 14.09.

IR $\nu_{max}$ cm$^{-1}$: 3000, 1705, 1600, 1580, 1430, 1380, 1340, 1305, 1060, 815.

EXAMPLE 1

Ethyl 7-(4-Acetyl-1-piperadinyl)-6-fluoro-4-oxo-4H[1,3]thiazeto[3,2-a]-1,8-naphthyridine-3-carboxylate A solution of 3.0 g of ethyl 7-(4-acetyl-1-piperazinyl)-6-fluoro-4-hydroxy-2-mercapto-1,8-naphthyridine-3-carboxylate was dissolved in 150 ml of chloroform and 50 ml of DMF was dropwise added to a solution obtained by heating and stirring a mixture comprising 4.08 g of methylene chloride, 2.54 g of potassium carbonate and 90 ml of DMF at 60° to 65° C., over a period of 2 hours. The whole solution was stirred for an additional 30 minutes at the same temperature and then water was added thereto. This was made weakly acidic with acetic acid and extracted with chloroform. The chloroform layer was separated, washed with water, dried and concentrated. Ethanol was added to the resulting residue, and the crystal formed was taken out by filtration and washed with a small amount of ethanol to obtain 2.87 g of a pale yellow crystal. m.p. 244° to 246° C. (decomposition).

EXAMPLE 2

6-Fluoro-7-(1-piperazinyl)-4-oxo-4H[1,3]-thiazeto[3,2-a]1,8-naphthyridine-3-carboxylic Acid Hydrochloride 3.6 g of the compound obtained in Example 1 was suspended in 36 ml of a 5% aqueous hydrochloric acid solution and heated and stirred at 100° C. for 4.5 hours. After it cooled, the crystal precipitated was taken out by filtration and washed with ethanol then ether. The crude crystal thus obtained was recrystallized from ethanol/water (1/1). Thus 2.1 g of a white powdery crystal was obtained. m.p. 235° C. (decomposition).

Elementary Analysis ($C_{14}H_{13}FN_4O_3S \cdot HCl$): Calculated Value (%) C: 45.11, H: 3.79, N: 15.03. Measured Value (%) C: 45.14, H: 3.84, N: 14.87.

EXAMPLE 3

6-Fluoro-7-(4-methyl-1-piperazinyl)-4-oxo-4H[1,3]-thiazeto[3,2-a]-1,8-naphthyridine-3-carboxylic Acid Hydrochloride 1.1 g of the compound obtained in Example 2 was suspended in 5 ml of water and neutralized with 2.35 ml of 5% sodium hydroxide. The crystal precipitated was taken out by filtration. This was washed with water, ethanol and ether in order. The crystal was dissolved in 3.6 ml of formic acid, and 1.2 ml of a 37% aqueous formalin solution was added thereto and heated and stirred for 1.5 hours at 110° to 120° C. After cooling this was diluted with ethanol and the crystal precipitated was taken out by filtration. The crystal was suspended in a small amount of water and then dissolved with a 5% aqueous sodium hydroxide solution. The resulting solution was made acidic with a 5% aqueous hydrochloric acid solution and then diluted with ethanol. The crystal precipitated was taken out by filtration and recrystallized from a mixed solvent of ethanol and water to obtain 0.84 g of a white powdery crystal. m.p. 240° C. (decomposition).

Elementary Analysis ($C_{15}H_{15}FN_4O_3S \cdot HCl$): Calculated Value (%) C: 46.57, H: 4.17, N: 14.48. Measured Value (%) C: 46.49, H: 4.14, N: 14.24.

EXAMPLE 4

(1) Diethyl 3-(5-chloro-6-morpholinylpyridin-2-yl)-[1,3]thiazetidin-2-ylidene-malonate While 4.10 g of methylene iodide, 2.54 g of potassium carbonate and 80 ml of dry DMF were heated and stirred at 50° to 60° C., a solution of 3.18 g of diethyl 5-chloro-6-morpholino-2-pyridinylaminomercaptomethylene-malonate dissolved in 160 ml of dry DMF was dropwise added thereto over a period of 6 hours. After the addition, the reaction mixture was concentrated under reduced pressure at 50° to 60° C., and the residue was dissolved in ethyl acetate, washed with water, dried and concentrated. N-hexane was added to the residue, and the crystal precipitated was recrystallized from n-hexane/ethyl acetate to obtain 2.01 g of a white crystal. m.p. 142° to 144° C.

(2) 6-Chloro-7-morpholino-4-oxo-4H-[1,3]-thiazeto[3,2-a]-1,8-naphthyridine-3-carboxylic acid While 40 g of fuming sulfuric acid was stirred under ice-cooling, 2.01 g of the compound obtained in the above-mentioned step (1) was gradually added thereto and stirred at room temperature for 12 hours. The reaction solution was added to water, and the colloidal crystal precipitate was taken out by centifugation. The crystal was washed with water and dried to obtain 1.10 g of a pale yellow crystal. m.p. 254° C. (decomposition).

Elementary Analysis ($C_{14}H_{12}ClN_3O_4S \cdot H_2O$) Calculated Value (%) C: 45.23, H: 3.79, N: 11.30. Measured Value (%) C: 45.51, H: 3.30, N: 11.29.

EXAMPLE 5

Ethyl 6-Chloro-1-methyl-7-morpholino-4-oxo-4H[1,3]thiazeto[3,2-a]-1,8-naphthyridine-3-carboxylate A solution of 6.10 g of ethyl 6-chloro-4-hydroxy-2-mercapto-7-morpholino-1,8-naphthyridine-3-carboxylate, 6.20 g of ethylidine bromide, 4.56 g of potassium carbonate and 66 mg of potassium iodide was dissolved in 660 ml of dry DMF was blended and heated with an oil bath of 100° to 110° C. for 5.5 hours with stirring. After the reaction, the reaction mixture was concentrated at 70° C. under reduced pressure. Ice-water was added to the residue, which was then extracted with chloroform. The chloroform layer was washed with water, dried and concentrated, and the residue thus obtained was crystallized with ethyl acetate. The crystal was taken out by filtration and recrystallized from ethyl acetate, to obtain 3.79 g of a pale yellow crystal. m.p. 192° to 193° C.

Elementary Analysis ($C_{17}H_{18}ClN_3O_4S$): Calculated Value (%) C: 51.58, H: 4.58, N: 10.62. Measured Value (%) C: 51.45, H: 4.63, N: 10.62.

EXAMPLE 6

6-Chloro-1-methyl-7-morpholino-4-oxo-4H[1,3]thiazeto[3,2-a]-1,8-naphthyridine-3-carboxylic Acid While 76 g of fuming sulfuric acid was stirred under ice-cooling, 3.79 g of the compound obtained in Example 5 was gradually added thereto and stirred at room temperature. After reacting for 12 hours, the reaction solution was added to ice, and the crystal precipitated was taken out by centrifugation. This was washed with water and dried to obtain 3.62 g of a crude crystal. This was recrystallized from DMF to obtain 2.44 g of a pale yellow crystal. m.p. 242° C. (decomposition).

Elementary Analysis ($C_{15}H_{14}ClN_3O_4S$): Calculated Value (%) C: 48.98, H: 3.84, N: 11.42. Measured Value (%) C: 48.78, H: 3.82, N: 11.16.

EXAMPLE 7

1-Methyl-7-(4-methyl-1-piperazinyl)-4-oxo-4H[1,3]thiazeto[3',2'-1,2]pyrido[2,3-d]pyrimidine-3-carboxylic Acid 0.300 g of the compound obtained in the step (3) of Referential Example was suspended in 10 ml of dry DMF. A solution of 0.212 g of N-methylpiperazine dissolved in 5 ml of dry DMF was dropwise added thereto at room temperature. After the addition, the solvent was removed by distillation under reduced pressure, and the residue was dissolved in chloroform. The insoluble substances were taken out by filtration and the solvent was removed by distillation under reduced pressure. The residue was recrystallized from ethanol to obtain 168 mg of the intended compound. m.p. 236° to 238° C. (decomposition).

Elementary Analysis ($C_{15}H_{17}N_5O_3S$): Calculated Value (%) C: 51.86, H: 4.93, N: 20.16. Measured Value (%) C: 51.47, H: 4.72, N: 19.88.

EXAMPLE 8

7-(4-Acetyl-1-piperazinyl)-1-methyl-4-oxo-4H[1,3]thiazeto[3',2'-1,2]pyrido[2,3-d]pyrimidine-3-carboxylic Acid 0.466 g of the compound obtained in the step (3) of Referential Example was suspended in 15 ml of dry DMF. A solution of 0.423 g of N-acetylpiperazine dissolved in 10 ml of dry DMF was dropwise added thereto at room temperature and stirred for 30 minutes. After the reaction, the solvent was removed by distillation under reduced pressure, and the crystal formed was washed with ethanol and dried under reduced pressure to obtain 0.39 g of the intended compound. m.p. 271° to 272° C. (decomposition).

Elementary Analysis ($C_{16}H_{17}N_5O_4S$): Calculated Value (%) C: 51.19, H: 4.56, N: 18.66. Measured Value (%) C: 51.02, H: 4.43, N: 18.46.

EXAMPLE 9

1-Methyl-7-(1-piperazinyl)-4-oxo-4H[1,3]thiazeto[3',2'-1,2]pyrido[2,3-d]pyrimidine-3-carboxylic Acid 257.5 mg of the compound obtained in Example 8 was suspended in 30 ml of 5% hydrochloric acid and refluxed for 3.5 hours. The reaction mixture was left as such overnight. The crystal precipitated was taken out by filtration, washed with ethanol and dried under reduced pressure to obtain 57.7 mg of the intended compound. m.p. 300° C. or higher.

Elementary Analysis ($C_{14}H_{15}N_5O_3S.HCl$): Calculated Value (%): C: 45.47, H: 4.36, N: 18.94. Measured Value (%): C: 45.22, H: 4.44, N: 18.80.

IR $\nu_{max}$ cm$^{-1}$: 3420, 2810, 2405, 1705, 1620, 1455, 1430, 1355, 1325, 1025, 810.

In the same manner as Examples 1 to 9, the following compounds were obtained.

EXAMPLE 10

Ethyl 7-(4-Acetyl-1-piperazinyl)-6-fluoro-1-methyl-4-oxo-4H[1,3]thiazeto[3,2-a]-1,8-naphthyridine-3-carboxylate m.p. 203° to 205° C.

Elementary Analysis ($C_{19}H_{21}FN_4O_4S$): Calculated Value (%) C: 54.28, H: 5.03, N: 13.33. Measured Value (%): C: 54.10, H: 5.04, N: 13.17.

EXAMPLE 11

Ethyl 7-(4-Acetyl-1-piperazinyl)-1-ethyl-6-fluoro-4-oxo-4H[1,3]thiazeto[3,2-a]-1,8-naphthyridine-3-carboxylate NMR δ (CDCl$_3$): 1.12(3H, t), 1.37(3H, t), 2.12(3H, s), 3.40~4.00(8H, m), 4.30(2H, q), 5.50~6.00(2H, m), 7.90(1H, d)

EXAMPLE 12

6-Fluoro-1-methyl-4-oxo-7-(1-piperazinyl)-4H[1,3]thiazeto[3,2-a]-1,8-naphthyridine-3-carboxylic Acid Hydrochloride m.p. 280° C. (decomposition).

Elementary Analysis ($C_{15}H_{15}FN_4O_3S.HCl$): Calculated Value (%) C: 46.57, H: 4.17, N: 14.48. Measured Value (%) C: 46.68, H: 4.10, N: 14.28.

EXAMPLE 13

1-Ethyl-6-fluoro-7-(1-piperazinyl)-4-oxo-4H[1,3]thiazeto[3,2-a]-1,8-naphthyridine-3-carboxylic Acid m.p. 207° to 209° C.

Elementary Analysis ($C_{16}H_{17}FN_4O_3S.4H_2O$): Calculated Value (%) C: 44.03, H: 5.77, N: 12.84. Measured Value (%) C: 43.75, H: 5.63, N: 12.86.

EXAMPLE 14

6-Fluoro-1-methyl-7-(4-methyl-1-piperazinyl)-4-oxo-4H[1,3]thiazeto[3,2-a]-1,8-naphthyridine-3-carboxylic Acid m.p. 250° to 252° C. (decomposition).

Elementary Analysis ($C_{16}H_{17}FN_4O_3S$): Calculated Value (%) C: 52.74, H: 4.70, N: 15.38. Measured Value (%) C: 52.81, H: 4.72, N: 14.91.

EXAMPLE 15

1-Ethyl-6-fluoro-7-(4-methyl-1-piperazinyl)-4-oxo-4H[1,3]thiazeto[3,2-a]-1,8-naphthyridine-3-carboxylic Acid m.p. 237° C.

Elementary Analysis ($C_{17}H_{19}FN_4O_3S.\frac{1}{2}H_2O$): Calculated Value (%) C: 52.70, H: 5.20, N: 14.46. Measured Value (%) C: 52.78, H: 4.76, N: 14.60.

EXAMPLE 16

Ethyl 7-(4-Ethoxycarbonyl-1-piperazinyl)-6-fluoro-4-oxo-4H[1,3]thiazeto[3,2-a]-1,8-naphthyridine-3-carboxylate m.p. 205° to 229° C. (decomposition).

Elementary Analysis ($C_{19}H_{21}FN_4O_5S$): Calculated Value (%) C: 52.29, H: 4.85, N: 12.84. Measured Value (%) C: 51.94, H: 4.92, N: 12.68.

EXAMPLE 17

Ethyl 6-Fluoro-1-methyl-7-morpholino-4-oxo-4H[1,3]thiazeto[3,2-a]-1,8-naphthyridine-3-carboxylate m.p. 198° to 202° C. (decomposition).

Elementary Analysis ($C_{17}H_{18}FN_3O_4S$): Calculated Value (%) C: 53.82, H: 4.78, N: 11.08. Measured Value (%) C: 53.64, H: 4.69, N: 10.92.

EXAMPLE 18

6-Fluoro-1-methyl-7-morpholino-4-oxo-4H[1,3]thiazeto[3,2-a]-1,8-naphthyridine-3-carboxylic Acid m.p. 249° C. (decomposition).

Elementary Analysis ($C_{15}H_{14}FN_3O_4S$): Calculated Value (%) C: 51.28, H: 4.02, N: 11.96. Measured Value (%) C: 51.30, H: 4.02, N: 11.68.

EXAMPLE 19

6-Fluoro-7-morpholino-4-oxo-4H[1,3]thiazeto[3,2-a]-1,8-naphthyridine-3-carboxylic Acid m.p. 280° to 283° C. (decomposition).

EXAMPLE 20

6-Chloro-4-oxo-7-(1-piperazinyl)-4H[1,3]thiazeto[3,2-a]-1,8-naphthyridine-3-carboxylic Acid Hydrochloride m.p. 250° C. (decomposition).

Elementary Analysis ($C_{14}H_{13}ClN_4O_3S.HCl$) Calculated Value (%) C: 43.20, H: 3.63, N: 14.39. Measured Value (%) C: 43.12, H: 3.39, N: 14.23.

EXAMPLE 21

6-Chloro-1-methyl-4-oxo-7-(1-piperazinyl)-4H[1,3]thiazeto[3,2-a]-1,8-naphthyridine-3-carboxylic Acid Hydrochloride m.p. 280° C. (decomposition).

Elementary Analysis ($C_{15}H_{15}ClN_4O_3S.HCl$): Calculated Value (%) C: 44.67, H: 4.00, N: 13.89. Measured Value (%) C: 44.69, H: 3.82, N: 13.72.

EXAMPLE 22

4-Chloro-7-(4-methyl-1-piperazinyl)-4-oxo-4H[1,3]thiazeto[3,2-a]-1,8-naphthyridine-3-carboxylic Acid m.p. 240° C. (decomposition).

Elementary Analysis ($C_{15}H_{15}ClN_4O_3S.H_2O$): Calculated Value (%) C: 46.82, H: 4.45, N: 14.56. Measured Value (%) C: 46.80, H: 4.34, N: 14.45.

EXAMPLE 23

6-Chloro-7-(4-methyl-1-piperazinyl)-4-oxo-4H[1,3]thiazeto[3,2-a]-1,8-naphthyridine-3-carboxylic Acid Ethanesulfonate m.p. 260° to 263° C.

EXAMPLE 24

6-Chloro-1-methyl-7-(4-methyl-1-piperazinyl)-4-oxo-4H-[1,3]thiazeto[3,2-a]-1,8-naphthyridine-3-carboxylic Acid m.p. 252° to 254° C. (decomposition).
Elementary Analysis ($C_{16}H_{17}ClN_4O_3S$): Calculated Value (%) C: 50.46, H: 4.50, N: 14.71. Measured Value (%) C: 50.36, H: 4.50, N: 14.58.

EXAMPLE 25

6-Chloro-1-methyl-7-(4-methyl-1-piperazinyl)-4-oxo-4H-[1,3]thiazeto[3,2-a]-1,8-naphthyridine-3-carboxylic Acid Ethanesulfonate m.p. 262° to 264° C.
Elementary Analysis ($C_{16}H_{17}ClN_4O_3S.C_2H_6O_3S.3/2H_2O$): Calculated Value (%) C: 41.74, H: 5.06, N: 10.82 Measured Value (%) C: 41.80, H: 5.18, N: 10.71

EXAMPLE 26

7-(4-Methyl-1-piperazinyl)-4-oxo-4H[1,3]thiazeto[3',2'-1,2]pyrido[2,3-d]pyrimidine-3-carboxylic Acid m.p. 300° C. or higher.
Elementary Analysis ($C_{14}H_{15}N_5O_3S$): Calculated Value (%) C: 50.44, H: 4.54, N: 20.52. Measured Value (%) C: 49.90, H: 4.72, N: 20.52.
IR $\nu_{max}$ cm$^{-1}$: 3400, 1695, 1620, 1465, 970, 805,

EXAMPLE 27

Ethyl 7-(4-Acetyl-1-piperazinyl)-6-chloro-4-oxo-4H[1,3]thiazeto[3,2-a]-1,8-naphthyridine-3-carboxylate NMR δ (CDCl$_3$): 1.33(3H, t), 2.11(3H, s) 3.30~3.90(8H,m), 4.29(2H, q), 5.38(2H, s), 8.32(1H, s).

EXAMPLE 28

Ethyl 7-(4-Acetyl-1-piperazinyl)-6-chloro-1-methyl-4-oxo-4H[1,3]thiazeto[3,2-a]1,8-naphthyridine-3-carboxylate NMR δ (CDCl$_3$): 1.35(3H, t), 2.12(3H, s) 2.13(3H, d), 3.20~3.90(8H,m), 4.30(2H, q) 5.94(1H, q), 8.32(1H, s).

EXAMPLE 29

Ethyl 7-(4-acetyl-1-piperazinyl)-6-fluoro-1-phenyl-4-oxo-4H[1,3]-1,8-naphthylidine-3-carboxylate. Mass analysis ($C_{24}H_{23}FN_4O_4S$), M+: 482.

EXAMPLE 30

Ethyl 7-(4-acetyl-1-piperazinyl)-6-fluoro-1-(4-fluorophenyl)-4-oxo-4H[1,3]thiazeto[3,2-a]1,8-naphthylidine-3-carboxylate. Mass analysis ($C_{24}H_{22}F_2N_4O_4S$), M+: 500.

EXAMPLE 31

Ethyl 7-(4-acetyl-1-piperazinyl)-1-(3,4-difluorophenyl)-6-fluoro-4-oxo-4H[1,3]thiazeto[3,2-a]-1,8-naphthylidine-3-carboxylate. Mass analysis ($C_{24}H_{21}F_3N_4O_4S$), M+: 518.

EXAMPLE 32

Ethyl 7-(4-acetyl-1-piperazinyl)-1-(2,4-difluorophenyl)-6-fluoro-4-oxo-4H[1,3]thiazeto[3,2-a]-1,8-naphthylidine-3-carboxylate. Mass analysis ($C_{24}H_{21}F_3N_4O_4S$), M+: 518.

EXAMPLE 33

Ethyl 7-(4-acetyl-1-piperazinyl)-1-(3,5-difluorophenyl)-6-fluoro-4-oxo-4H[1,3]thiazeto[3,2-a]-1,8-naphthylidine-3-carboxylate. Mass analysis ($C_{24}H_{21}F_3N_4O_4S$), M+: 518.

EXAMPLE 34

6-Fluoro-1-phenyl-7-piperazinyl-4-oxo-4H-oxo[1,3]-thiazeto[3,2-a]-1,8-naphthylidine-3-carboxylic acid hydrochloride. M.p. 250° C. (decompn.). Mass analysis ($C_{20}H_{17}FN_4O_3S.HCl$), M+: 448.
Elementary analysis for $C_{20}H_{17}FN_4O_3S.HCl.H_2O$: Calcd: C 51.45, H 4.31, N 12.00. Found: C 51.43, H 4.10, N 12.19.

EXAMPLE 35

6-fluoro-1-(4-flurophenyl)-7-piperadinyl-4-oxo-4H(1,3)thiazeto(3,2-a)-1,8-naphthylidine-3-carboxylic acid. M.p. 260° C. (decompn.). Mass analysis ($C_{20}H_{16}F_2N_4O_3S$), M+: 430.
Elementary analysis for $C_{20}H_{16}F_2N_4O_3S.2H_2O$ Calcd (%): C 51.50, H 4.32, N 12.01. Found (%): C 49.91, H 4.19, N 12.63.

EXAMPLE 36

1-(2,4-diflurophenyl)-6-fluoro-7-piperadinyl-4-oxo-4H(1,3)thiazeto(3,2-a)-1,8-naphthylidine-3-carboxylic acid. M.p. 230° C. (decompn). Mass analysis ($C_{20}H_{15}F_3N_4O_3S$), M+: 448.
Elementary analysis for $C_{20}H_{15}S_3N_4O_3S.H_2O$ Calcd (%) C 51.50, H 43.67, N 12.01; Found (%) C 51.31, H 3.67, N 11.54.

EXAMPLE 37

1-(3,4-diflurophenyl)-6-fluoro-7-piperadinyl-4-oxo-4H(1,3)thiazeto(3,2-a)-1,8-naphthylidine-3-carboxylic acid. Mass analysis ($C_{20}H_{15}F_3N_4O_3S$), M+: 448.

EXAMPLE 38

1-(3,5-diflurophenyl)-6-fluoro-7-piperadinyl-4-oxo-4H(1,3)thiazeto(3,2-a)-1,8-naphthylidine-3-carboxylic acid. Mass analysis ($C_{20}H_{15}F_3N_4O_3S$), M+: 448.

EXAMPLE 39

6-fluoro-7-(4-methyl-1-piperadinyl)-1-phenyl-4-oxo-4H(1,3)thiazeto(3,2-a)-1,8-naphthylidine-3-carboxylic acid. M.p. 270° C. (decompn.). Mass analysis ($C_{21}H_{19}FN_4O_3S$), M+: 426.

EXAMPLE 40

6-fluoro-1-(4-fluorophenyl)-7-(4-methyl-1-piperadinyl)-4-oxo-4H(1,3)thiazeto(3,2-a)-1,8-naphthylidine-3-carboxylic acid. M.p. 270° C. (decompn.). Mass analysis ($C_{21}H_{18}F_2N_4O_3S$), M+: 444.
Elementary analysis for $C_{21}H_{18}F_2N_4O_3S.H_2O$ Calcd (%): C 54.54, H 4.36, N 12.11. Found (%): C 54.88, H 4.51, N 11.37.

EXAMPLE 41

1-(3,4-difluorophenyl)-6-fluoro-7-(4-methyl-1-piperadinyl)-4-oxo-4H(1,3)thiazeto(3,2-a)-1,8-naphthylidine-3-carboxylic acid. Mass analysis ($C_{21}H_{19}F_3N_4O_3S$), M+: 502.

EXAMPLE 42

1-(2,4-diflurophenyl)-6-fluoro-7-(4-methyl-1-piperadinyl)-4-oxo-4H(1,3)thiazeto(3,2-a)-1,8-naphthylidine-3-carboxylic acid. Mass analysis ($C_{21}H_{19}F_3N_4O_3S$), M+: 502.

EXAMPLE 43

1-(3,5-diflurophenyl)-6-fluoro-7-(4-methyl-1-piperadinyl)-4-oxo-4H(1,3)thiazeto(3,2-a)-1,8-naphthylidine-3-carboxylic acid. Mass analysis ($C_{21}H_{19}F_3N_4O_3S$), M+: 502.

EXAMPLE 44

Ethyl 6-fluoro-7-(4-methyl-1-piperadinyl)-1-phenyl-4-oxo-4H(1,3)thiazeto(3,2-a)-1,8-naphthylidine-3-carboxyalte A mixture of 200 mg of the compound obtained in Example 39, 64 mg of potassium carbonate, 74 mg of ethyl iodide and 6 ml of N,N-dimethylformamide were stirred at room temperature for 16 hours. 60 ml of water was added to the reaction mixture and then extracted with chloroform. The chloroform layer was washed with water; dried and then concentrated and the resultant residue was purified on silica gel chromatography to obtain 120 mg of crystals. M.p. 197°–198° C. Mass analysis ($C_{23}H_{23}FN_4O_3S$), M+: 454.

Elementary analysis for $C_{23}H_{23}FN_4O_3S.\frac{1}{2}H_2O$ Calcd (%): C 59.60, H 5.21, N 12.09; Found (%) C 59.69, H 5.15, N 11.99

The following compounds were obtained in the same manner as in Example 44.

EXAMPLE 45

Ethyl 6-fluoro-1-(4-fluorophenyl)-7-(4-methyl-1-piperadinyl)-4-oxo-4H(1,3)thiazeto(3,2-a)-1,8-naphthylidine-3-carboxyalte. Mass analysis ($C_{23}H_{22}F_2N_4O_3S$), M+: 472.

EXAMPLE 46

Ethyl 1-(3,4-difluorophenyl)-6-fluoro-7-(4-methyl-1-piperadinyl)-4-oxo-4H(1,3)thiazeto(3,2-a)-1,8-naphthylidine-3-carboxylate. Mass analysis ($C_{23}H_{21}F_3N_4O_3S$), M+: 490.

EXAMPLE 47

Ethyl 1-(2,4-difluorophenyl)-6-fluoro-7-(4-methyl-1-piperadinyl)-4-oxo-4H(1,3)thiazeto(3,2-a)-1,8-naphthylidine-3-carboxylate. Mass analysis ($C_{23}H_{21}F_3N_4O_3S$), M+: 490.

EXAMPLE 48

Ethyl 1-(3,5-difluorophenyl)-6-fluoro-7-(4-methyl-1-piperadinyl)-4-oxo-4H(1,3)thiazeto(3,2-a)-1,8-naphthylidine-3-carboxylate. Mass analysis ($C_{23}H_{21}F_3N_4O_3S$), M+: 490.

EXAMPLE 49

1-(2,4-diflurophenyl)-6-fluoro-7-(4-(5-methyl-2-oxo-1,3-dioxolan-4-yl)methyl-1-piperadinyl)-4-oxo-4H(1,3)thiazeto(3,2-a)-1,8-naphthylidine-3-carboxylic acid 449 mg of the compound obtained in Example 36, 120 mg of potassium hydrogen carbonate were suspended in 5 ml of N,N-dimethylformamide, to which 232 mg of 4-bromomethyl-5-methyl-1,3-dioxolan-4-one was dropped under ice cooling and stirred for 3 hours. After the reaction was over, the solvent was distilled off at 60° C. under a reduced pressure. Iced water was added to the resultant residue and insoluble matters were collected by filtration, washed with water and then dried in air. Crude crystals were recrystallized from a chloroform-methanol mixed solution to obtain an aimed product. M.p. 215° C. (decompn) Mass analysis ($C_{25}H_{19}F_3N_4O_3S$), M+: 560.

Elementary analysis for $C_{25}H_{19}F_3N_4O_6S$. Cacld (%): C 53.57, H 3.42, N 10.00; Found (%) C 52.86, H 3.53, N 9.78.

The following compounds were obtained in the same manner as in Example 49.

EXAMPLE 50

6-fluoro-7-(4-(5-methyl-2-oxo-1,3-dioxolan-4-yl)methyl-1-piperadinyl)-1-phenyl-4-oxo-4H(1,3)thiazeto(3,2-a)-1,8-naphthylidine-3-carboxylic acid. Mass analysis ($C_{25}H_{21}FN_4O_6S$), M+: 524.

EXAMPLE 51

6-fluoro-1-(4-fluorophenyl)-7-(4-(5-methyl-2-oxo-1,3-dioxolan-4-yl)methyl-1-piperadinyl)-1-phenyl-4-oxo-4H(1,3)thiazeto(3,2-a)-1,8-naphthylidine-3-carboxylic acid. Mass analysis ($C_{25}H_{20}F_2N_4O_6S$), M+: 542.

EXAMPLE 52

1-(3,4-diflurophenyl)-6-fluoro-7-(4-(5-methyl-2-oxo-1,3-dioxolan-4-yl)methyl-1-piperadinyl)-4-oxo-4H(1,3)thiazeto(3,2-a)-1,8-naphthylidine-3-carboxylic acid. Mass analysis ($C_{25}H_{19}F_3N_4O_3S$), M+: 560.

EXAMPLE 53

1-(3,5-diflurophenyl)-6-fluoro-7-(4-(5-methyl-2-oxo-1,3-dioxolan-4-yl)methyl-1-piperadinyl)-4-oxo-4H(1,3)thiazeto(3,2-a)-1,8-naphthylidine-3-carboxylic acid. Mass analysis ($C_{25}H_{19}F_3N_4O_3S$), M+: 560.

EXAMPLE 54

Ethyl 6-fluoro-1-(4-fluorophenyl)-7-piperadinyl-4-oxo-4H(1,3)thiazeto(3,2-a)-1,8-naphthylidine-3-carboxylate 430 mg of the compound obtained in Example 35 was dissolved in 15 ml of 95% formic acid, to which 5 ml of anhydrous acidic acid was dropped under ice cooling and stirring. After stirring the reaction mixture at room temperature for 4 hours, it was poured into iced water and deposited crystals were collected by filtration, washed with water and ethanol and then dried. Then, a mixture of the resultant crystals, 138 mg of potassium carbonate, 156 mg of methyl iodide and 10 ml of N,N-dimethylformamide was stirred at room temperature over one night. 100 ml of water was added to the reaction solution and extracted with chloroform. The chloroform layer was washed with water, dried and then concentrated. Successively, 12 ml of ethanol and 0.24 ml of concentrated sulfuric acid were added to the resultant residue and then refluxed under temperatures of 80°–90° C. for 4.5 hours. After condensation the reaction solution under a reduced pressure, 10 ml of water was added, neutralized with sodium hydrogen carbonate and then extracted with chloroform. The chloroform layer was washed with water, dried and then concentrated under a reduced pressure. The residue was purified on silica gel chromatography to obtain the abovecaptioned compound. Mass analysis ($C_{22}H_{20}F_2N_4O_3S$), M+: 458.

The following compounds were obtained in the same manner as in Example 54.

EXAMPLE 55

Ethyl 6-fluoro-1-phenyl-7-piperadinyl-4-oxo-4H(1,3)thiazeto(3,2-a)-1,8-naphthylidine-3-carboxylate. Mass analysis ($C_{22}H_{21}FN_4O_3S$), M+: 440.

EXAMPLE 56

Ethyl 1-(3,4-difluorophenyl)-6-fluoro-7-piperadinyl-4-oxo-4H(1,3)thiazeto(3,2-a)-1,8-naphthylidine-3-carboxylate. Mass analysis ($C_{22}H_{19}F_3N_4O_3S$), M+: 476.

EXAMPLE 57

Ethyl 1-(2,4-difluorophenyl)-6-fluoro-7-piperadinyl-4-oxo-4H(1,3)thiazeto(3,2-a)-1,8-naphthylidine-3-carboxylate. Mass analysis ($C_{22}H_{19}F_3N_4O_3S$), M+: 476.

EXAMPLE 58

Ethyl 1-(3,5-difluorophenyl)-6-fluoro-7-piperadinyl-4-oxo-4H(1,3)thiazeto(3,2-a)-1,8-naphthylidine-3-carboxylate. Mass analysis ($C_{22}H_{19}F_3N_4O_3S$), M+: 476.

PHARMACEULOGICAL DATA

Compounds representative of the present invention were tested in order to demonstrate the antibacterial activity of the compounds of the present invention.

1. Measurement of Minimal Growth Inhibitory Concentration (MIC)

Test Method:

MIC was measured by agar plate dilution assay method in accordance with the standard by Japan Chemical Therapeutics Association (refer to Journal of Japan Chemical Therapeutics Association, 29 (1), 76 to 79 (1981).

Briefly, a bacteria suspension as incubated in a bouillon medium for measurement of sensitivity, at 37° C. for 18 hours was diluted to $10^6$ CFU/ml with the same medium. This was inoculated on an agar medium for measurement of sensitivity, which contained a compound to be tested, with a microplanter and incubated at 37° C. for 18 hours and then the MIC was measured. Enoxacin was used as a control. The results obtained are set forth in Table 1 below. As is clear therefrom, the compounds of the present invention had an extremely strong bactericidal activity against *Pseudomonas aeruginosa* and other gram-positive bacteria and gram-negative bacteria.

The compounds of the present invention demonstrate a marked antibacterial activity in particular against *P. aeruginosa* E-2 wherein the compounds of the present invention showed a higher level of activity than shown by enoxacin.

2. Remedial Effect Against Mouse Infectious Diseases

Test Method:

*E. coli* KC-14 and *P. aeruginosa* E-2 each were suspended in 4% muchin, and 0.25 ml of each of the resulting suspensions was inoculated into the abdominal cavity of ddy male mice (weight: about 20 g, 4-week age, 10 mice for one group). The amount of the bacteria inoculated was $5.1 \times 10^4$ CFU/mouse for *E. coli* KC-14 and y$7.5 \times 10^4$ CFU/mouse for *P. aeruginosa* E-2. Two hours after the inoculation of the bacteria, the compound to be tested was orally administered once, and the number of the animals living after one week was counted. The results obtained were compared with those using the control enoxacin. The results are set forth in Table 1 below.

The compounds of the present invention had a strong remedial effect on mouse infectious diseases, in particular, the activity against *P. aeruginosa* E-2 was higher than enoxacin which is strongly effective against that bacteria.

The compounds of the present invention are particularly useful for treating urinary tract infections and chologenic tract infections.

TABLE 1

| Compound of Example No. | MIC (μg/ml) | | | Remedial Effect | |
|---|---|---|---|---|---|
| | (1) | (2) | (3) | (2) | (3) |
| 14 | 0.1 | 0.0125 | 0.2 | + + + | + + + |
| 2 | 0.39 | 0.05 | 0.39 | + | + |
| 3 | 0.39 | 0.025 | 0.39 | + + + | + + + |
| 12 | 0.1 | 0.0125 | 0.1 | + + + | + + + |
| 20 | 0.78 | 0.05 | 0.78 | + | − |
| 21 | 0.39 | 0.025 | 0.78 | + | + |
| 25 | 0.39 | 0.025 | 0.78 | + | − |
| 18 | 0.1 | 0.05 | 0.78 | + | − |
| 7 | 1.56 | 0.1 | 1.56 | + + | − |
| | 0.78 | 0.2 | 0.78 | + + | + + |
| Enoxacin | | | | | |
| 34 | 0.39 | 0.1 | 0.39 | | |
| 35 | 0.39 | 0.1 | 0.39 | | |

(1) means *S. aureus*; (2) means *E. coli*; and (3) means *P. aerug*. (−) means ineffective; (+) means somewhat poorer than enoxacin; (+ +) means comparable to enoxacin; and (+ + +) means extremely effective.

What is claimed is:

1. A compound of the formula

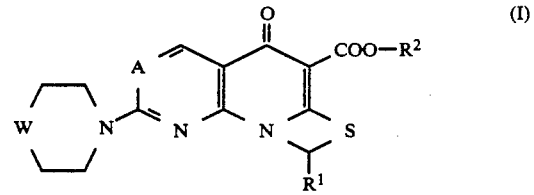

or a pharmaceutically acceptable salt thereof wherein $R^1$ is hydrogen, lower alkyl or phenyl unsubstituted or substituted by one or two halo moieties, $R_2$ is hydrogen or lower alkyl, A is N, W is O or $NR_3$ wherein $R^3$ is hydrogen, lower alkyl, acyl, mono-, di- or tri-haloacyl, lower alkoxycarbonyl or (5-methyl-2-oxo-1,3-dioxolen-4-yl) methyl.

2. A compound according to claim 1 wherein $R^1$ is hydrogen.

3. A compound according to claim 1 wherein $R^1$ is lower alkyl.

4. A compound according to claim 1 wherein $R^2$ is hydrogen.

5. A compound according to claim 1 wherein $R^2$ is lower alkyl.

6. A compound according to claim 1 wherein $R_2$ is phenyl unsubstituted or substituted by one or two fluoro moieties.

7. A compound according to claim 1 wherein W is O.

8. A compound according to claim 1 wherein W is $NR^3$, wherein $R^3$ is hydrogen, lower alkyl, straight or branch chain acyl of 1 to 6 carbon atoms unsubstituted or trifluoro substituted, alkoxycarbonyl of 2 to 5 carbon atoms or (5-methyl-2-oxo-1,3-dioxolen-4-yl) methyl.

9. A compound according to claim 1 in the form of a pharmaceutically acceptable salt.

10. A pharmaceutical composition useful for treating bacterial infections in humans and animals which comprises an antibacterially effective amount of a compound of the formula

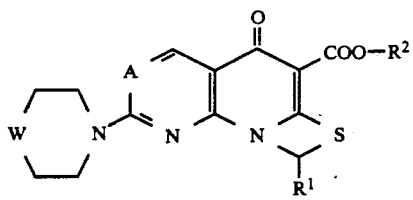

or a pharmaceutically acceptable salt thereof wherein $R^1$ is hydrogen, lower alkyl or phenyl unsubstituted or substituted by one or two halo moieties, $R_2$ is hydrogen or lower alkyl, A is N, W is O or $NR_3$ wherein $R^3$ is hydrogen, lower alkyl, acyl, mono-, di- or tri-haloacyl, lower alkoxycarbonyl or (5-methyl-2-oxo-1,3-dioxolen-4-yl) methyl, in combination with a pharmaceutically acceptable carrier.

11. A composition according to claim 10 wherein $R^1$ is hydrogen.

12. A composition according to claim 10 wherein $R^1$ is lower alkyl.

13. A composition according to claim 10 wherein $R^2$ is hydrogen.

14. A composition according to claim 10 wherein $R^2$ is lower alkyl.

15. A composition according to claim 10 wherein $R_1$ is phenyl unsubstituted or substituted by one or two fluoro moieties.

16. A composition according to claim 10 wherein W is O.

17. A composition according to claim 10 wherein W is $NR^3$, wherein $R^3$ is hydrogen, lower alkyl, straight or branch chain acyl of 1 to 6 carbon atoms unsubstituted or trifluoro substituted, alkoxycarbonyl of 2 to 5 carbon atoms or (5-methyl-2-oxo-1,3-dioxolen-4-yl) methyl.

18. A composition according to claim 10 wherein the compound is in the form of a pharmaceutically acceptable salt.

19. A method of treating bacterial infections in humans and animals which comprises administering to a human or animal in need thereof an antibacterially effective amount of a compound of the formula

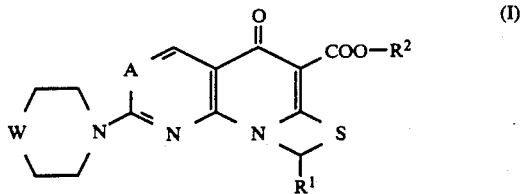

or a pharmaceutically acceptable salt thereof wherein $R^1$ is hydrogen, lower alkyl or phenyl unsubstituted or substituted by one or two halo moieties, $R^2$ is hydrogen or lower alkyl, A is N, W is O or $NR^3$ wherein $R^3$ is hydrogen, lower alkyl, acyl, mono-, di- or tri-haloacyl, lower alkoxycarbonyl or (5-methyl-2-oxo-1,3-dioxolen-4-yl) methyl, in combination with a pharmaceutically acceptable carrier.

20. A method according to claim 19 wherein $R^1$ is hydrogen.

21. A method according to claim 19 wherein $R^1$ is lower alkyl.

22. A method according to claim 19 wherein $R^2$ is hydrogen.

23. A method according to claim 19 wherein $R^2$ is lower alkyl.

24. A method according to claim 19 wherein $R^1$ is phenyl unsubstituted or substituted by one or two fluoro moieties.

25. A method according to claim 19 wherein W is O.

26. A method according to claim 19 wherein W is $NR_3$, wherein $R^3$ is hydrogen, lower alkyl, straight or branch chain acyl of 1 to 6 carbon atoms unsubstituted or trifluoro substituted, alkoxycarbonyl of 2 to 5 carbon atoms or (5-methyl-2-oxo-2,3-dioxolen-4-yl) methyl.

27. A method according to claim 19 wherein the compound is in the form of a pharmaceutically acceptable salt.

* * * * *